United States Patent
Bachim et al.

(10) Patent No.: US 7,352,474 B2
(45) Date of Patent: Apr. 1, 2008

(54) INTERFEROMETRIC OPTICAL TOMOGRAPHY

(75) Inventors: Brent L. Bachim, Smyrna, GA (US); Thomas K. Gaylord, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 496 days.

(21) Appl. No.: 11/040,418

(22) Filed: Jan. 21, 2005

(65) Prior Publication Data

US 2005/0157312 A1 Jul. 21, 2005

Related U.S. Application Data

(60) Provisional application No. 60/538,119, filed on Jan. 21, 2004.

(51) Int. Cl.
*G01B 11/02* (2006.01)
(52) U.S. Cl. ........................... 356/512; 356/497
(58) Field of Classification Search ............... 356/73.1, 356/479, 497, 489, 495, 511–515; 250/227.11
See application file for complete search history.

(56) References Cited

U.S. PATENT DOCUMENTS 5,798,840 A * 8/1998 Beiting ........................ 356/437

OTHER PUBLICATIONS

Gorski and Kujawinska. "Three-dimensional reconstruction of refractive index inhomogeneities in optcial phase elements" Optics and Lasers in Engineering 38 (2002) pp. 373-385.*
Brent L. Bachim and Thomas K. Gaylord; "Micro-Interferometric Optical Phase Tomography for Measuring Small, Asymmetric Refractive Index Differences in the Profiles of Optical Fibers and Fiber Devices;" Applied Optics, vol. 44, Issue 3, Jan. 2005; pp. 316-327.
W.J. Stewart; "Optical Fiber and Preform Profiling Technology;" IEEE Journal of Quantum Electronics, vol. QE-18, No. 10, Oct. 1982; pp. 1451-1466.
Maksymilian Pluta; "Profile Refractometry of Optical Fibers by Using Double-Refracting Microinterferometry;" Gradient-Index Optics in Science and Engineering, 1996; pp. 113-127.
K.W. Raine, J.G.N. Baines, and D.E. Putland; "Refractive Index Profiling-State of the Art;" Journal of Lightwave Technology, vol. 7, No. 8, Aug. 1989; pp. 1162-1169.
Yasuo Kokubun and Kenichi Iga; "Precise Measurement of the Refractive Index Profile of Optical Fibers by a Nondestructive Interference Method;" The Transactions of the IECE of Japan, vol. E60, No. 12, Dec. 1977; pp. 702-707.

(Continued)

*Primary Examiner*—Patrick Connolly
(74) *Attorney, Agent, or Firm*—Thomas, Kayden, Horstemeyer & Risley, LLP

(57) ABSTRACT

Embodiments of the present disclosure provide systems and methods for constructing a profile of sample object. Briefly described, in architecture, one embodiment of the system, among others, can be implemented as follows. An interferometer device is used to collect interference images of a sample object at a sequence of angles around the sample object. Accordingly, a controller device rotates the sample object to enable acquisition of the interference images; and a projection generator produces projections of the sample object from the interference images at the sequence of angles. Further, a tomographic device constructs the profile of the optical device from the projections of the interference images. The profile is capable of characterizing small index variations of less than $1 \times 10^{-4}$. Other systems and methods are also included.

20 Claims, 8 Drawing Sheets

OTHER PUBLICATIONS

D. Marcuse and H.M. Presby; "Focusing Method for Nondestructive Measurement of Optical Fiber Index Profiles;" Applied Optics, vol. 18, No. 1, Jan. 1979; pp. 14-22.

Takanori Okoshi and Masayuki Nishimura; "Measurement of Axially Nonsymmetrical Refractive-Index Distribution of a Single-Mode Fiber by a Multidirectional Scattering-Pattern Method;" Journal of Lightwave Technology, vol. LT-1, No. 1, Mar. 1983; pp. 9-14.

J. Stone and H.E. Earl; "Optical Fiber Refractometry by Interference Microscopy: A Simplified Method;" Applied Optics, vol. 17, No. 22, Nov. 1978; pp. 3647-3652.

Kenji Toga, Nobuo Amano, and Ken-Ichi Noda; "Microscopic Computer Tomography Measurement of Nonaxisymmetrically Distributed Optical Fiber Refractive Index;" Journal of Lightwave Technology, vol. 6, No. 1, Jan. 1988; pp. 73-79.

Dale Alicia Viskoe and Gregory W. Donohoe; "Optimal Computed Tomography Data Acquisition Techniques and Filter Selection for Detection of Small Density Variations;" IEEE Transactions on Instrumentation and Measurement, vol. 45, No. 1, Feb. 1996; pp. 70-76.

Qian Zhong and Daryl Inniss; "Characterization of the Lightguiding Structure of Optical Fibers by Atomic Force Microscopy;" Journal of Lightwave Technology, vol. 12, No. 9, Sep. 1994; pp. 1517-1523.

H.M. Presby, D. Marcuse, H.W. Astle, and L.M. Boggs; "Rapid Automatic Index Profiling of Whole-Fiber Samples: Part II;" The Bell System Technical Journal, Apr. 1979; pp. 883-903.

Malgozata Sochacka; "Optical Fibers Profiling by Phase-Stepping Transverse Interferometry;" Journal of Lightwave Technology, vol. 12, No. 1, Jan. 1994; pp. 19-23.

Shane T. Huntington, Ann Roberts, Keith A. Nugent, and Simon C. Fleming; "Complete Characterization of a High-Numerical-Aperature Small-Core Fiber with Subwavelength Resolution Using Atomic Force Microscopy and Near-Field Scanning Optical Microscopy;" Society of Photo-Optical Instrumentation Engineers, 2003; pp. 1893-1895.

S.T. Huntington, P. Mulvaney, A. Roberts, K.A. Nugent, and M. Bazylenko; "Atomic Force Microscopy for the Determination of Refractive Index Profiles of Optical Fibers and Waveguides: A Quantitative Study;" J. Appl. Phys., Sep. 1997; pp. 2730-2734.

Witold Górski; "The Influence of Diffraction in Microinterferometry and Microtomography of Optical Fibers;" Opt. Lasers Engineering, 2004; pp. 563-583.

Witold Górski and Malgorzata Kujawińska; "Three-Dimensional Reconstruction of Refractive Index Inhomogeneities in Optical Phase Elements;" Opt. Lasers Engineering, 2002; pp. 373-385.

Norman H. Fontaine and Matt Young; "Two-Dimensional Index Profiling of Fibers and Waveguides;" Applied Optics, vol. 38, No. 33; pp. 6836-6844.

Kokou Dossou, Sophie LaRochelle, and Marie Fontain; "Numerical Analysis of the Contribution of the Transverse Asymmetry in the Photo-Induced Index Change Profile to the Birefringence of Optical Fiber;" Journal of Lightwave Technology, vol. 20, No. 8, Aug. 2002; pp. 1463-1470.

L.M. Boggs, H.M. Presby, and D. Marcuse; "Rapid Automatic Index Profiling of Whole-Fiber Sample: Part I;" The Bell System Technical Journal, vol. 58, No. 4, Apr. 1979; pp. 867-883.

A. Barty, K.A. Nugent, A. Roberts, and D. Paganin; "Quantitative Phase Tomography;" Opt. Lasers Engineering, Mar. 2000; pp. 329-336.

N. Barakat, H.A. El-Hennawi, E.Abd. El-Ghafar, H. El-Ghandoor, R. Hassan, F. El-Diasty; "Three-Dimensional Refractive Index Profile of a GRIN Optical Waveguide Using Multiple Beam Interference Fringes;" Opt. Lasers Engineering, May 2001; pp. 39-47.

E. Anemogiannis, E.N. Glytsis, and T.K. Gaylord; "Transmission Characteristics of Long-Period Fiber Gratings Having Arbitrary Azimuthal/Radial Refractive Index Variations;" Journal of Lightwave Technology, vol. 21, No. 1, Jan. 2003; pp. 218-227.

Zhongyao Liu, Xiaoman Dong, Qianghua Chen, Chunyong Yin, Yuxian Xu, and Yingjun Zheng; "Nondestructive Measurement of an Optical Fiber Refractive-Index Profile by a Transmitted-Light Differential Interference Contact Microscope;" Applied Optics, vol. 43, No. 7, Mar. 2004; pp. 1485-1492.

\* cited by examiner

INTERFEROMETRIC OPTICAL TOMOGRAPHY

CROSS-REFERENCE TO RELATED APPLICATION

This application claims priority to copending U.S. provisional application entitled, "Micro Interferometric Optical Computed Tomography," having Ser. No. 60/538,119, filed Jan. 21, 2004, which is entirely incorporated herein by reference.

TECHNICAL FIELD

The present disclosure is generally related to computer tomography and, more particularly, is related to measuring the physical properties of optical objects using computer tomography.

BACKGROUND

The refractive-index profile of optical fiber devices is of critical importance for determining the subsequent performance of optical fibers and fiber devices. For example, the refractive-index profile of dispersion-compensating optical fiber is tailored to achieve specific levels of dispersion at telecommunication wavelengths. As another example, polarization-maintaining optical fiber relies on circular asymmetry present in the fiber structure to decouple orthogonal polarization states. Moreover, small, irregular index variations can also impact optical fiber and fiber devices—this is especially true if such variations lead to asymmetry in the transverse refractive-index profile. Varied indices of refraction can also cause birefringence in optical fiber devices, which alters transmission spectra and introduces polarization dependent loss.

Most refractive-index profiling techniques are designed to measure optical fiber devices with azimuthally symmetric (axisymmetric) refractive-index profiles. This includes both higher resolution interferometric and non-interferometric techniques. Of the techniques capable of two-dimensional index profiling, they either lack sufficient index resolution for characterizing certain devices (such as quantitative phase imaging) or are destructive (such as etching-atomic force microscopy). Thus, an alternative system capable of high-resolution refractive-index profiling of azimuthally asymmetric optical fiber (devices) is desired.

SUMMARY

Embodiments of the present disclosure provide systems and methods for constructing a profile of sample object. Briefly described, in architecture, one embodiment of the system, among others, can be implemented as follows. An interferometer device is used to collect interference images of a sample object at a sequence of angles around the sample object. Accordingly, a controller device rotates the sample object to enable acquisition of the interference images; and a projection generator produces projections of the sample object from the interference images at the sequence of angles. Further, a tomographic device constructs the profile of the optical device from the projections of the interference images. The profile is capable of characterizing small index variations of less than $1\times10^{-4}$ for the sample object.

Embodiments of the present disclosure can also be viewed as providing methods for constructing a profile of a sample object. In this regard, one embodiment of such a method, among others, can be broadly summarized by the following steps: acquiring multiple projections around a range exceeding 180 degrees around the sample object; and constructing a profile of the sample object from the multiple projections, wherein the profile is capable of characterizing small index variations of less than $1\times10^{-4}$ for the sample object.

Other systems, methods, features, and advantages of the present disclosure will be or become apparent to one with skill in the art upon examination of the following drawings and detailed description. It is intended that all such additional systems, methods, features, and advantages be included within this description and be within the scope of the present disclosure.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Correct modeling of transmission spectra of optical fiber devices (e.g., optical fiber, fiber gratings, other phase objects, etc.) possessing arbitrary azimuthal/radial refractive-index variations requires knowledge of the transverse refractive-index profile of the devices. For example, knowledge of the form of the index asymmetry is pertinent to reducing birefringence during fabrication of optical devices. Therefore, to understand and predict the impact of small, asymmetric index variations (about $1\times10^{-4}$), the refractive-index profiles of an optical device needs to be accurately measured. As such, it is also desirable to be able to measure the index profile of an optical fiber device in a non-destructive manner to facilitate testing of the optical fiber device.

Accordingly, embodiments of the present disclosure include a measurement technique based on microinterferometry and tomography for use in multi-dimensional profiling optical fibers and fiber devices with small, asymmetric index variations over the cross-sectional profile of small objects, such as optical fibers and fiber devices, including elliptical core polarization-maintaining fiber, twin-core optical fiber, fiber exposed to ultraviolet- or carbon-dioxide-laser light, fiber couplers, cleaved fiber endfaces, and fiber fusion splices, among others.

Microinterferometric optical phase tomography (MIOPT), combines the high resolution, high accuracy measurement capabilities (both in spatial and refractive-index terms) of interferometry with the ability to profile irregular objects provided by computed tomography. Thus, the spatial resolution gained by using microinterferometry allows profiling of samples with more rapidly varying radial changes, as occurs in dispersion-compensating fiber, for example. Therefore, embodiments of the present disclosure produce multi-dimensional profiling of irregular objects through the measurement of a set of projections via computed tomography (e.g., parallel projection based computed tomography).

Figure 1:
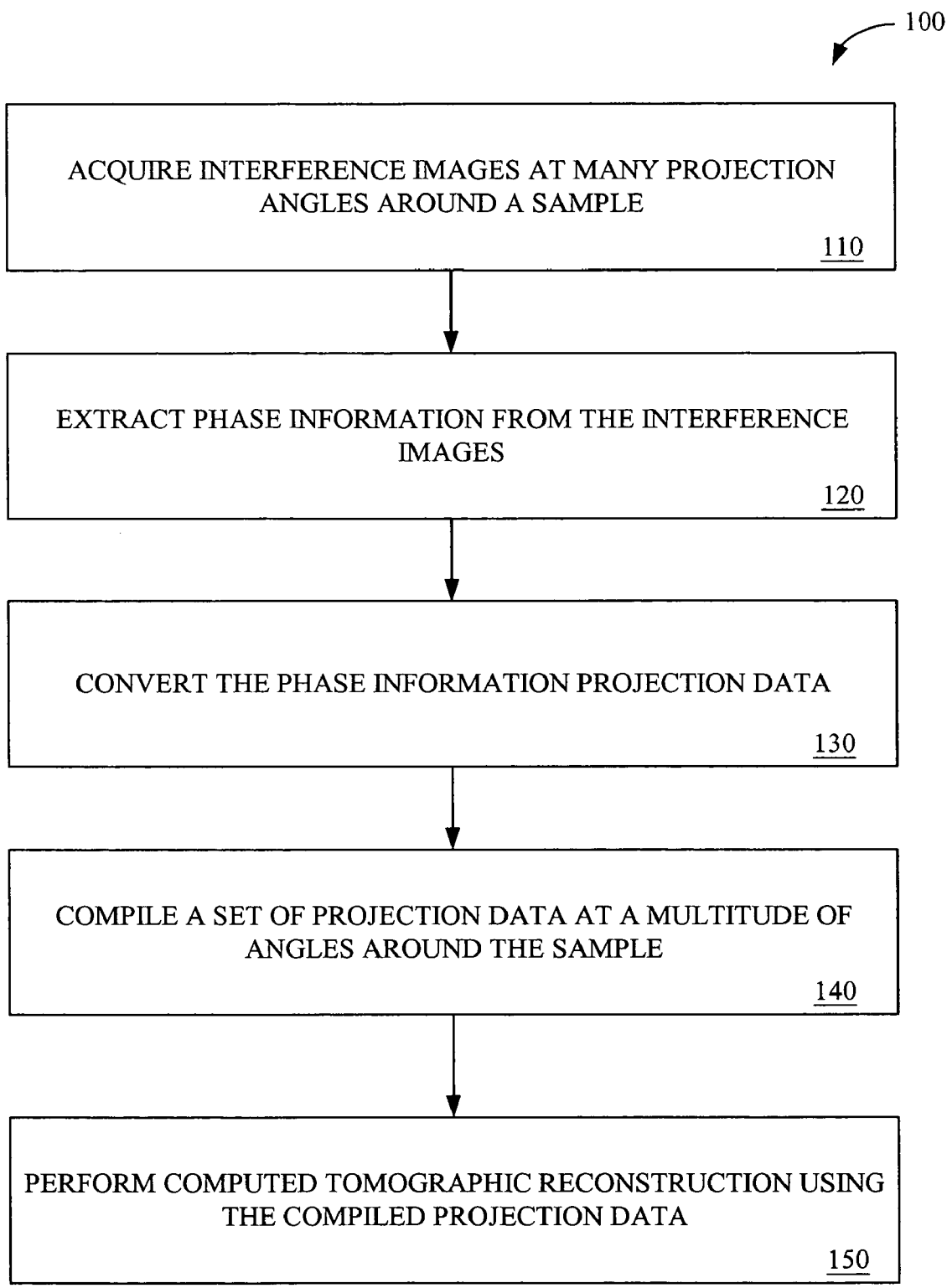
FIG. 1 is one embodiment, among others, of a microinterferometric optical phase tomography (MIOPT) process of the present disclosure.

FIG. 1 and subsequent figures show different embodiments of MIOPT processes. The flowchart of FIG. 1, for example, shows the functionality and operation of a possible implementation of the MIOPT process for one embodiment, among others. In this regard, each block represents a step for implementing a particular embodiment of the MIOPT process. It should also be noted that in some alternative implementations, the functions noted in the blocks may occur out of the order noted in FIG. 1 (and subsequent figures). For example, two blocks shown in succession in one figure may in fact be executed substantially concurrently or the blocks may sometimes be executed in the reverse order in another embodiment, depending upon the functionality involved, as will be appreciated by one of ordinary skill in the art.

Referring back to FIG. 1, one embodiment of the MIOPT process (100) includes the steps of acquiring (110) interference images at many projection angles around a sample (e.g., optical fiber) and extracting (120) phase information from the interference images. The phase information is converted (130) into projection data, where a set or sequence of projection data is compiled (140) at a multitude of angles around the sample. Computed tomographic reconstruction is then performed (150) using the compiled projection data. Each of the steps is discussed in detail below.

In FIG. 1, the first step involves measuring or acquiring (110) interference images at a set of projection angles around an optical fiber sample (or other device of interest). In particular, a projection measurement is conducted by recording interference images of an optical fiber sample at different angles around the longitudinal axis (relative to fiber) using an interference microscope, in some embodiments. Due to the large number of images that are to be collected, the measurement process is automated. In addition, due to lengthy reconstruction times, projection data may be acquired, stored, and then processed at a later time.

A set of one-dimensional projection measurements is to be collected. Generally, an individual projection is a one-dimensional representation of an object that contains both intrinsic property and spatial information. Moreover, in the context of measuring refractive-index profiles, a projection is a line integral ("projection integral") of the object's refractive index taken at a specific angle around the object and over its spatial extent. Such a projection can be interpreted as the optical path length over its spatial extent when the object is viewed at a particular angle. Projections are used to reconstruct a two-dimensional transverse index profile. In other embodiments, however, three-dimensional measurements (addition of longitudinal direction) can be formed by stacking two-dimensional reconstructed profiles.

The projection integral can be calculated from phase information extracted (120) from an interference image or interferogram of an object or sample. Projections, obtained from interference images, contain information about the sample refractive index encountered by rays traversing the fiber cross-section, for example. Therefore, while projections cannot be measured directly using nondestructive techniques, they can be calculated from the accumulated phase differences of rays that travel through the sample. In alternative embodiments, other techniques may also be employed to obtain projection data, such as those involving wave transmissions.

One way to measure the phase is by interfering a sample beam (or optical wave), that passes through the object, with a reference beam (or reference wave). Such interferometric techniques are non-destructive and possess good index accuracy and resolution. For example, interference measurement schemes routinely detect optical path differences of less than $\lambda/100$ and thus can detect small changes in index for the same path length. Numerous techniques exist for generating interference images of phase objects. In particular, static fringe-field interferometry is considered in some embodiments The static interferogram analysis technique selected for use, in some embodiments, employs a direct polynomial fitting routine based on parabolic approximation of fringe minima. This approach has the advantage of requiring only one interference image per projection for calculating the phase. Accordingly, a threshold is first applied to the images to locate approximately the fringe minima. Data below the threshold level is then retained for use in polynomial fitting. Each pixel column of an interference image is treated as an individual ray for calculation purposes. Therefore, the fitting routine is used to identify fringe minima pixel locations along each column. Once the minima locations are known, the relative index projection can be calculated. All images captured during measurement are analyzed to extract their phase, which is used to calculate the projection.

Figure 2:
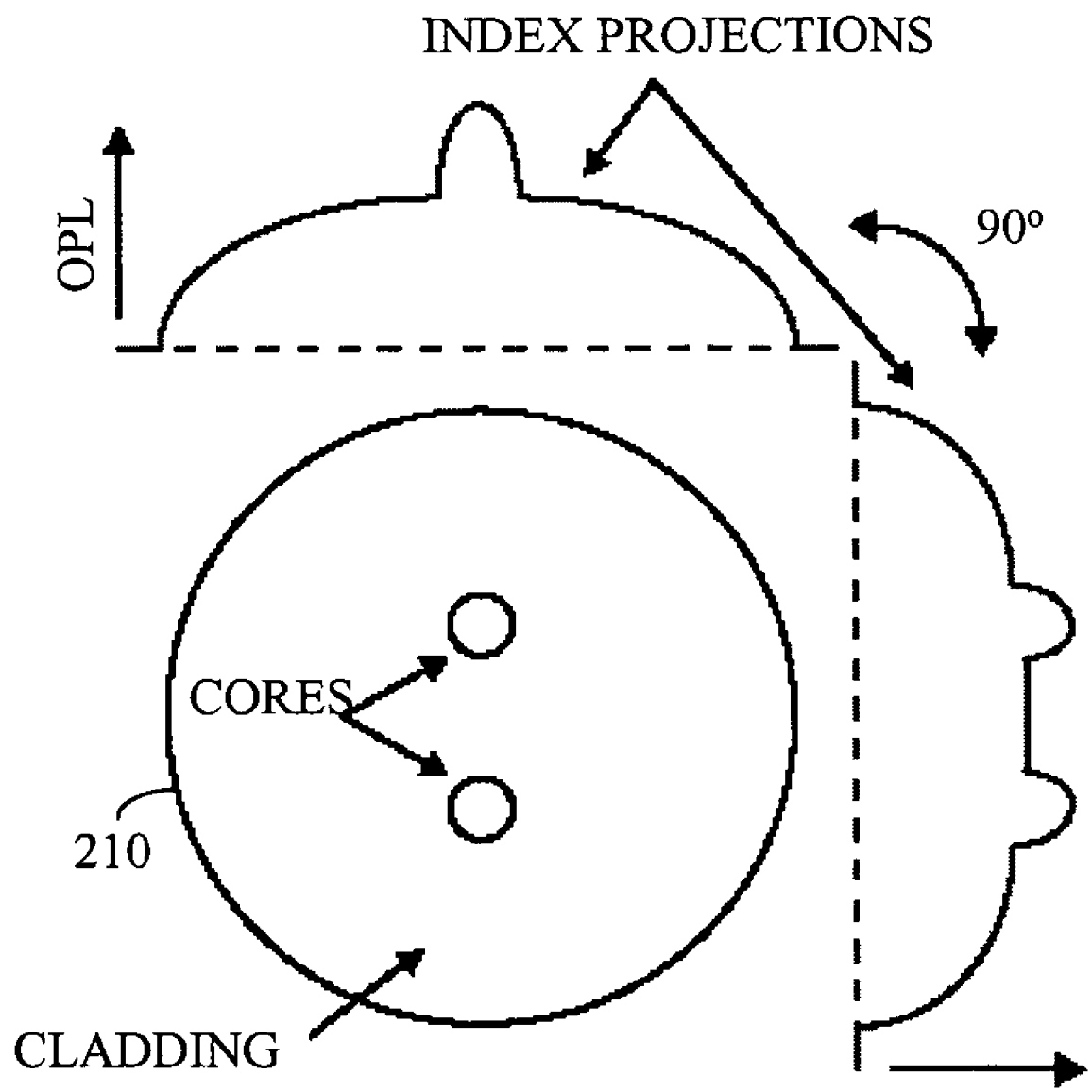
FIG. 2 is a diagram illustration of refractive-index projections of a twin-core optical fiber to aid in further understanding the process of FIG. 1.
Figure 3:
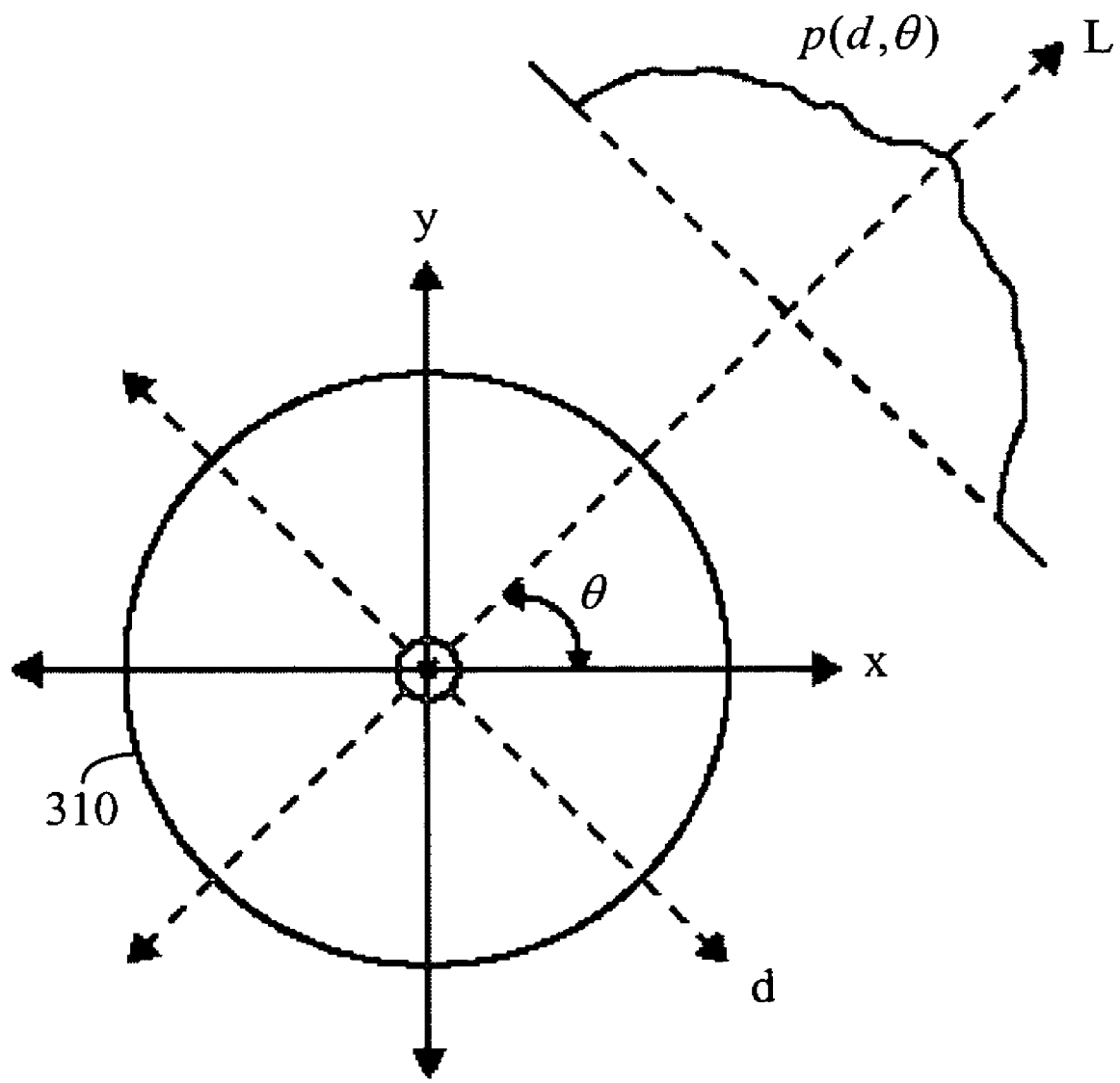
FIG. 3 is a diagram representing the relationship between fixed coordinate system of the optical fiber of FIG. 2 and a rotated coordinate system of a projection.

To illustrate, the concept of a projection is illustrated in FIG. 2 and the notation used in discussing them in FIG. 3. In particular, FIG. 2 represents an illustration of refractive-index projections of a twin core optical fiber 210, and FIG. 3 is a diagram representing the relationship between fixed coordinate system of the optical fiber 310 and the rotated coordinate system of the projection. Therefore, the d and L axes represent the rotated coordinate system of the projection and are related to the fixed coordinate system of the object (x and y axes) by the projection angle θ. In mathematical terms, a projection, p(d,θ), taken at a particular angle (θ) from the x-axis is:

$$p(d, \theta) = \int_{-\infty}^{\infty} n(d, L) dL, \tag{1}$$

with n(d, L) being the refractive-index profile of the object in the rotated coordinate system. The profile n(d, L) is related to n(x, y) by a transformation involving the angle θ.

In some embodiments, parallel projections are exclusively considered for use in measuring two-dimensional profiles possessing small index differences. This places a condition on rays traveling through the test object. Namely, no refraction should occur. The absence of refraction implies that rays traveling through the sample cross-section are perpendicular to the d-axis in the rotated coordinate system at every projection angle. Although index difference exists in optical fibers (at least at the core-cladding interface), and this causes some rays to be refracted, refraction at the outer boundaries is limited if the refractive index of the surrounding matching oil is closely matched to the sample cladding (e.g., within $1 \times 10^{-3}$) in an interference microscope system. Other measures can also be taken to limit refraction effects and are discussed hereinafter. After proper practices are adopted, this parallel projection approximation for ray travel is valuable in characterizing fiber samples (or other optical devices) with small index differences.

Figure 4:
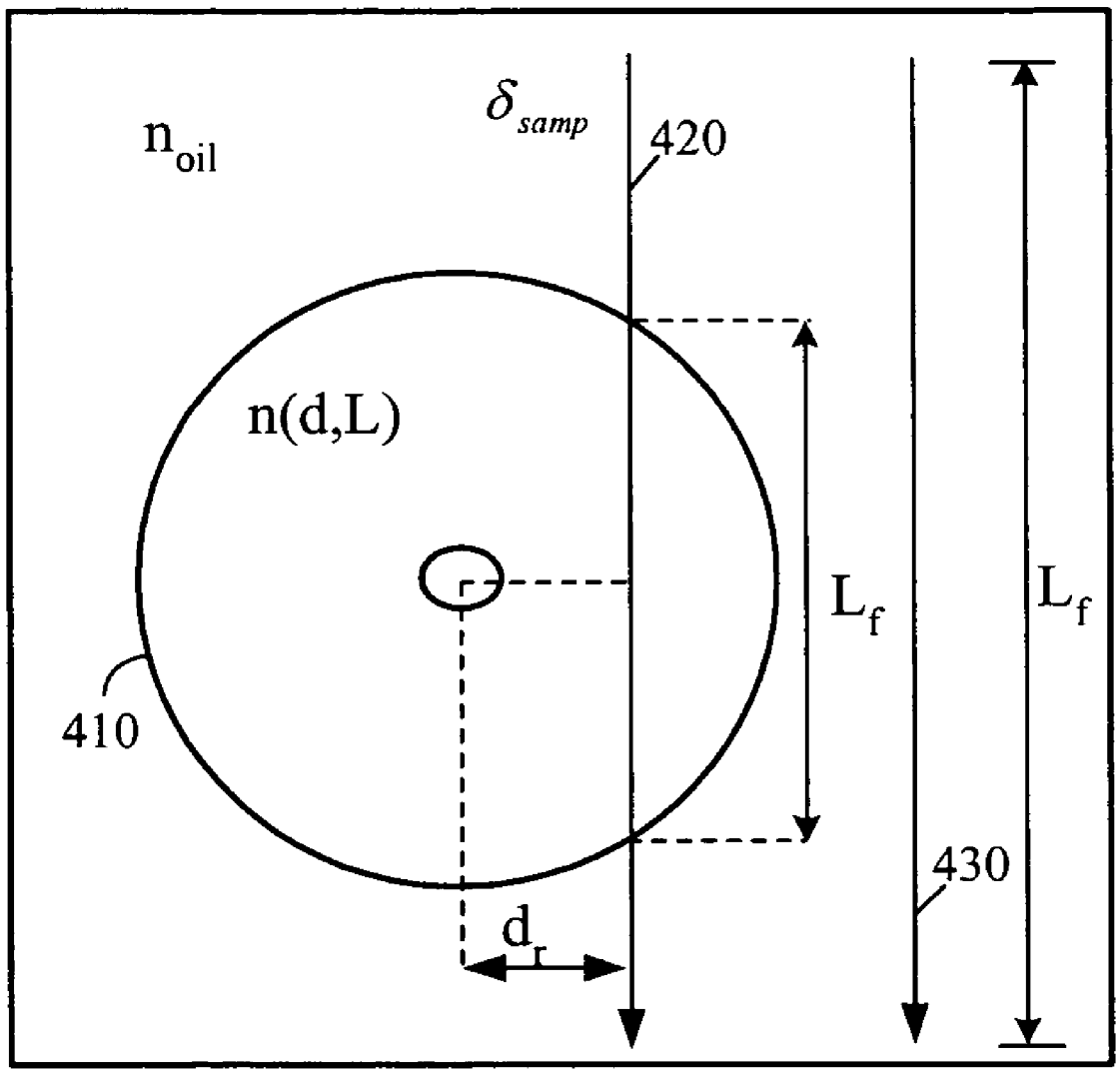
FIG. 4 is a diagram showing a ray passing through an optical fiber sample to aid in further understanding the process of FIG. 1

FIG. 4 shows a ray passing through an optical fiber sample 410. The figure depicts a transverse cross-section of a typical single-mode optical fiber, but could also represent another object or device with a more complicated profile. Only one ray is shown in the illustration, although a collection of rays at points along the d-axis is necessary to obtain one projection at each angle θ. The following equations are developed for a ray 420 passing perpendicularly (to the d-axis) through the object 410, as occurs in the rotated projection coordinate system and are correct for any angle. The mathematical relationship between the measured phase from the interferogram and the projection integral is developed below through examination of the accumulated phase of rays in the sample and reference arms of an interferometer. The accumulated phase of a ray passing through the optical fiber in the sample arm of the interferometer, $\delta_{samp}$, is given by:

$$\delta_{samp} = k_o n_{oil}[L_r - L_f] + k_o \int_{L_f} n(d, L) dL, \quad (2)$$

where $k_o$ is the free-space wavevector magnitude; $n_{oil}$ is the refractive index of the matching oil; $L_r$ is an arbitrary reference length; $L_f$ is the length of the sample which the ray traverses (with $L_r > L_f$), and $n(d, L)$ is the two-dimensional refractive-index profile of the optical fiber sample in the rotated coordinate system. The accumulated phase of a matching ray 430 in the reference arm of the interferometer, $\delta_{ref}$, is simply:

$$\delta_{ref} = k_o n_{oil} L_r = k_o n_{oil}[L_r - L_f] + k_o n_{oil} L_f \quad (3)$$

As the waves in the two interferometer arms interfere, the phase differences between the sample and reference result in relative shifts in the minimum/maximum intensity peaks of the static interferogram. The phase difference between rays in the reference and sample beams that pass through the matching oil equals zero and their interference peaks serve as the baseline for calculating the phase shift due to the presence of the sample. The phase difference between reference rays and rays traveling through the sample are calculated by subtracting equations (2) and (3). This difference is interpreted as the relative phase shift ($\Delta\delta$), with:

$$\Delta\delta = \delta_{samp} - \delta_{ref} \quad (4)$$

$$= k_o n_{oil}[L_r - L_f] + k_o \int_{L_f} n(d, L) dL -$$

$$k_o n_{oil}[L_r - L_f] - k_o n_{oil} L_f,$$

$$\Delta\delta = k_o \int_{L_f} n(d, L) dL - k_o n_{oil} L_f. \quad (5)$$

Accordingly, the phase information is converted (130) into projection data. For each angle, the recorded interferogram is analyzed to yield the one-dimensional index projection of the sample. For the type of object under consideration, a projection represents the refractive-index line integral of a set of rays traveling through the same object. With a sequence of projections or a measured projection data set, an object's two dimensional refractive-index profile can then be reconstructed through the use of various algorithms. Numerous computed tomography algorithms exist for reconstructing objects from measured projections, including the commonly-implemented filtered backprojection algorithm.

The resulting integral term in Equation (5) is the projection required for directly implementing computed tomography reconstruction to retrieve the index profile. However, a different form of the integral is more conducive to performing the reconstruction. The alternative form can be derived by rewriting the $n_{oil}$ term in Equation (5) as:

$$k_o n_{oil} L_f = k_o \int_{L_f} n_{oil} dL. \quad (6)$$

The integral term in Equation (6) can then be substituted into Equation (5) to yield:

$$\Delta\delta = k_o \int n(d, L) dL - k_o \int_{L_f} n_{oil} dL \quad (7)$$

$$= k_o \int_{L_f} [n(d, L) - n_{oil}] dL.$$

The integral term containing the difference between $n(d, L)$ and $n_{oil}$ can be calculated directly from a recorded interference image and confers the advantage of eliminating the need to calculate $L_f$ during analysis and reconstruction. Although the relative refractive index is being reconstructed, simply adding the refractive index of the matching oil after the reconstruction process yields the desired sample refractive index, $n(x, y)$.

To calculate the relative refractive-index projection integral from interference image data, the relative fringe shift is measured from the baseline fringes that do not pass through the sample and the fringe separation distance. The relative phase shift, $\Delta\delta$, at some distance, $d_r$, from the fiber core is calculated from the interferogram using:

$$\Delta\delta = \frac{2\pi Q_d}{D}, \quad (8)$$

where $Q_d$ is the distance from the baseline fringe reference and D is the separation distance between fringe minima (or maxima) and represents a $2\pi$ difference.

The integral term containing the difference between $n(d, L)$ and $n_{oil}$ can be calculated directly from a recorded interference image and confers the advantage of eliminating the need to calculate $L_f$ during analysis and reconstruction. Although the relative refractive index is now being reconstructed, simply adding the refractive index of the matching oil after the reconstruction process yields the desired sample refractive index, n(x, y).

A set or sequence of projection data is compiled (140) at a multitude of angles around the optical device. A set of projections consists of individual projection measurements taken at various angles around the test object. From a set of m projections, the object refractive-index profile can be reconstructed $$n(x, y) = \int_0^{2\pi} d\theta \int_0^{\infty} P(w, \theta) w e^{i2\pi w d} \, dw, \quad (9)$$

with w being the spatial frequency and P(w,θ) being the Fourier transform of the projection p(d,θ). For example, in some embodiments, the set of all projections over 360 degrees around an optical device is used to reconstruct the two-dimensional refractive-index profile and each projection can be calculated from the phase shift derived from an interferogram. The full projection data set serves as the input to the computed tomography reconstruction algorithm.

Equating Equations (5) and (6) and then rearranging them gives the relative refractive-index projection integral in terms of the quantities measured from the interference images taken at each projection angle, $$p_r(d, \theta) = \int_{L_f} [n(d, L) - n_{oil}] dL = \frac{2\pi Q_d}{k_o D} = \frac{Q_d}{D} \lambda_o, \quad (10)$$

where $p_r(d,\theta)$ is now the relative-index projection. Since the physical path is the same, the integral also represents the optical path difference along the d-axis. A set of relative projections taken at various angles around the test object can be used to reconstruct the relative-index profile, from which the actual index profile can be determined by adding the matching oil refractive-index value.

Figure 5:
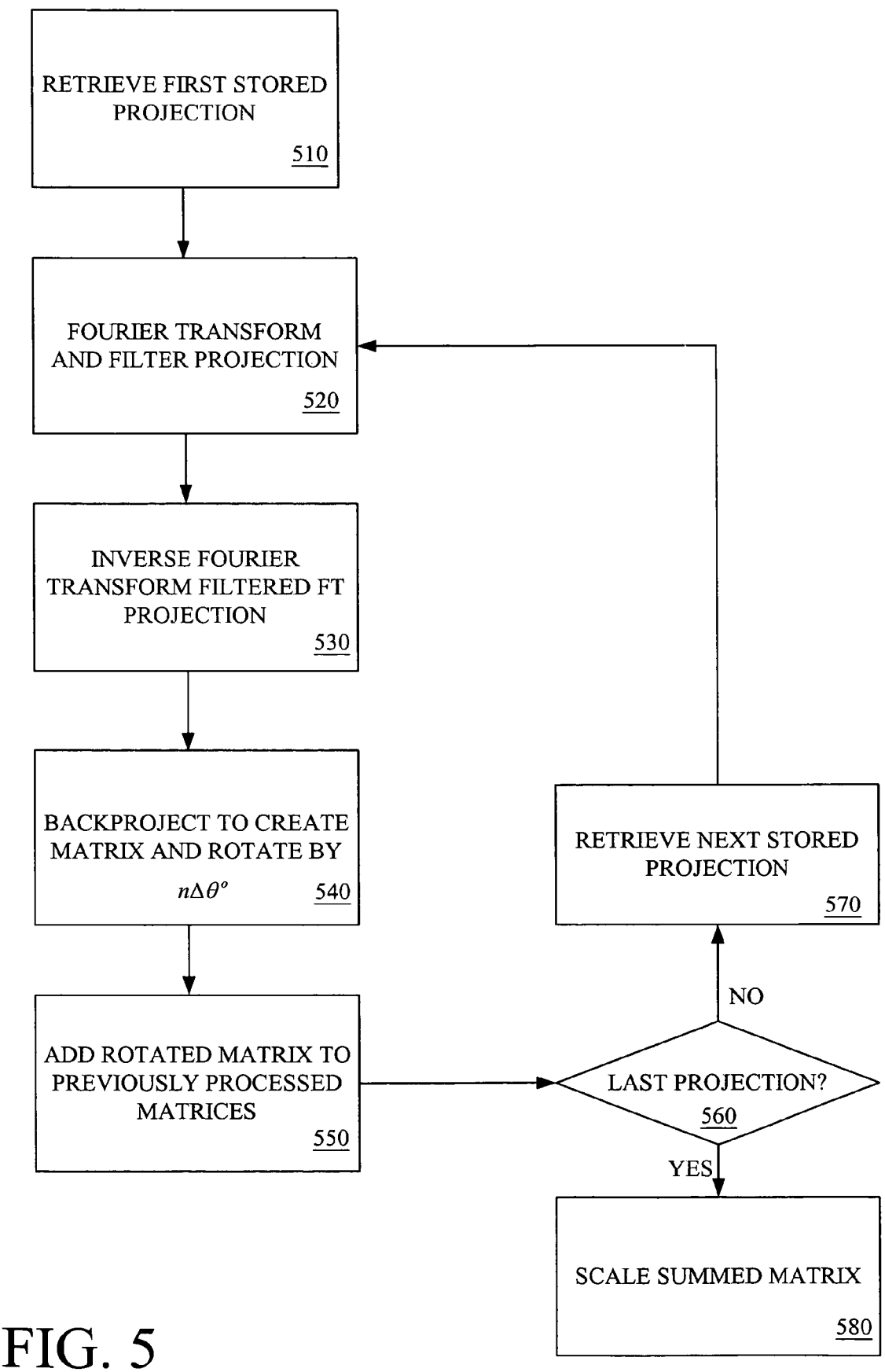
FIG. 5 is a flowchart diagram of one embodiment, among others, of a reconstruction procedure, as utilized in the process of FIG. 1.

Correspondingly, computed tomography reconstruction is then performed (150). In some embodiments, tomographic reconstruction, is implemented using the filtered backprojection algorithm, although other reconstruction algorithms do exist and are utilized in different embodiments. One benefit of the filtered backprojection algorithm is that it provides flexibility for optimizing the reconstruction process to increase accuracy. In this process, as shown in FIG. 5, a first stored projection is retrieved (510) and then, a Fourier transform is first performed (520) for each measured projection, from the full projection data. Further, a reconstruction filter (e.g., a frequency domain ramp-type filter) is applied. Note, by modifying the basic ramp-type reconstruction filter used in the filtered backprojection algorithm, selected spatial frequencies are attenuated. Thus, modifying the filter can be useful when attempting to profile fibers with small index variations in, for instance, the cladding region.

Following the filtering operation, an inverse Fourier transform is performed (530). The now filtered projection is backprojected (540) to create a square matrix (m×m, with m the number of image columns in the interferogram), which is then rotated by a corresponding projection angle nΔθ°, where n is the sequential number of the projection (e.g., 1-720).

All of the filtered, backprojected, and rotated matrices are summed (550), then scaled, to form the reconstructed object. Zero-padding is performed at appropriate points during the procedure. Object reconstruction is complete (560-580) when all projections have been processed from the full projection data, and the matching oil's index value is added to the reconstructed profile to retrieve the index profile n(x, y).

Figure 6:
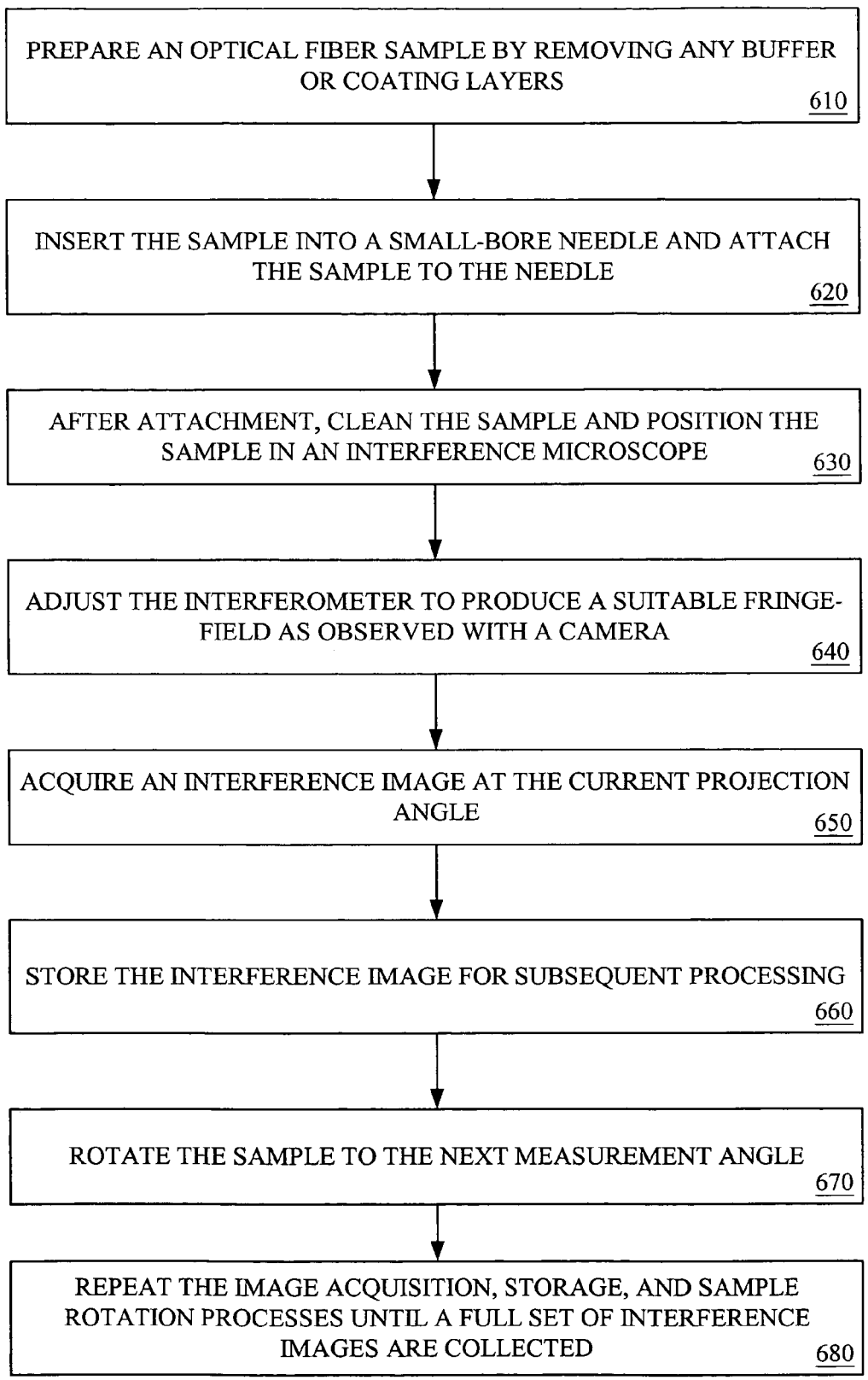
FIG. 6 is a flowchart diagram of one embodiment, among others, of the MIOPT process of FIG. 1.

Referring now to FIG. 6, another embodiment of the MIOPT process is presented. First, an optical fiber sample is prepared (610) for profiling by first removing any buffer or coating layers. The sample is then inserted (620) into a small-bore needle and attached to the needle with a small amount of adhesive. After attachment, the sample is cleaned and then positioned (630) in the sample arm of an interference microscope. The interferometer is then adjusted (640) to produce a suitable fringe-field as observed with a camera.

Following initial sample preparation, an interference image is acquired (650) at the current projection angle, stored (660) for subsequent processing, and the sample rotated (670) to the next measurement angle. Periodically, acquisition is temporarily halted and the microscope focus is adjusted to ensure the sample remains correctly focused. The image acquisition, storage, and sample rotation process is repeated (680) until a full set of interference images are collected (e.g., over 360 degrees around the sample at every 1 degree around the sample, for some embodiments).

Note, it is important for the sample to rotate about its longitudinal axis without wobble, deviation, or displacement, such effects degrade the accuracy of the reconstructed object. Thus, a motorized rotation stage, under the control of a motion controller, rotates an optical fiber sample around its longitudinal axis to enable acquisition of interference images at a sequence of angles around the sample. A program running on the computer is responsible for instrument control (stage movement, image acquisition) and image processing (for calculating projection data).

After collecting a full set of interference images for the fiber sample, image processing techniques are used to identify (690) the fringe minima locations in each image. The index projections required for reconstructing the cross-sectional refractive-index profile of the sample are derived from the identified minima locations. After processing of interference images, ambient temperature variations that may occur during measurement are corrected, in some embodiments. The reconstructed profiles are shown relative to the surrounding refractive index of the matching oil used during measurement [n(x, y)–$n_{oil}$].

For example, in an illustrative experiment, the quantitative features of a reconstructed cross-sectional refractive-index profile of a sample bow-tie type polarization-maintaining fiber (PMF), agreed well with the qualitative features observed in the dark-field reflected-light image of a polished endface of the PMF. From the reconstructed refractive-index profile, the stress-producing region of the PMF was also evident in its profile. Further, the cladding diameter in the reconstructed profile closely matched the PMF's specified value. Noise in the profile was relatively low and the typical tomographic starring effect, while present, was minor. The low levels of both resulted from practices implemented in MIOPT during measurement and reconstruction. Particularly evident in both the profile and image was the slant of the outer edges of the bow-tie region and the distortion at the corners.

Embodiments of the MIOPT process can also be used to profile optical fibers with azimuthally symmetric cross-sectional refractive-index profiles. Although tomography is not required for profiling symmetric objects, its application can advantageously lower overall noise levels and potentially reveal index irregularities and other unintended non-uniformities. For instance, in an illustrative experiment, the cladding and core diameters in a reconstructed profile of a standard telecommunications single-mode optical fiber (SMF) closely matched the SMF's specified values. Further, in comparison with a common one-dimensional profiling technique, the reconstructed profile was similar to the common profile and possessed lower noise levels.

Based on the two index profiles measured by embodiments of the MIOPT process in the two illustrative experiments above, the estimated spatial resolution was 0.5 µm while the index resolution was estimated to be below (better than) $1 \times 10^{-5}$. Thus, the example measured profiles demonstrate the ability of MIOPT to profile both azimuthally asymmetric and symmetric optical fibers or fiber devices. Accordingly, the technique is suitable for characterizing samples such as optical fiber exposed to laser light and fluid-filled microstructure and photonic-crystal fiber. The advantages of using MIOPT for profiling include lower noise levels and higher resolution, both of which are important for accurate characterization of intentional or unintentional small and/or irregular index variations. Further, modifications of the set-up apparatus and implementation of more sophisticated processing algorithms can improve accuracy and reduce starring (or other) artifacts, in some embodiments. In addition, three-dimensional refractive-index profiles [n(x, y, z)] of optical fibers and other optical devices can be obtained by stacking two-dimensional cross-sectional profiles. In some embodiments, the spatial resolution in the longitudinal (z) direction is set by the spacing of parallel, consecutive fringes present in the interference image and approaches $1 \times 10^{-5}$ meters.

Embodiments of the MIOPT process can be implemented in a variety of arrangements. A microinterferometer arrangement, with associated hardware, is typically preferred for obtaining interference images of optical fiber and fiber devices to perform profiling. While it is possible to construct an apparatus for conducting measurements from bulk optical elements, several interference microscopes already exist that are suitable for use in the system. The Mach-Zehnder two-objective, transmitted-light interference microscope, traditionally used for profiling symmetric optical fibers, is adapted to enable interference measurements at various angles, in some embodiments.

Use of a developed commercial interference microscope, as opposed to a bulk optic interferometer implementation, offers several advantages for conducting the types of measurement performed in the present disclosure. Interference microscopes, such as the Mach-Zehnder transmitted-light system, are designed to have precise, stable optical elements that minimize wavefront distortion and maintain path balance and thereby increase interference image stability. Optical plates and wedges incorporated within the microscope permit precise adjustment of fringe spacing, orientation, and width. The ability to conduct precise adjustments means that fringe properties can be optimized for detecting small index differences. Spurious fringes and speckle noise are reduced by using a bright, bandpass-filtered mercury lamp instead of a laser-based illumination system commonly employed in bulk systems.

Figure 7:
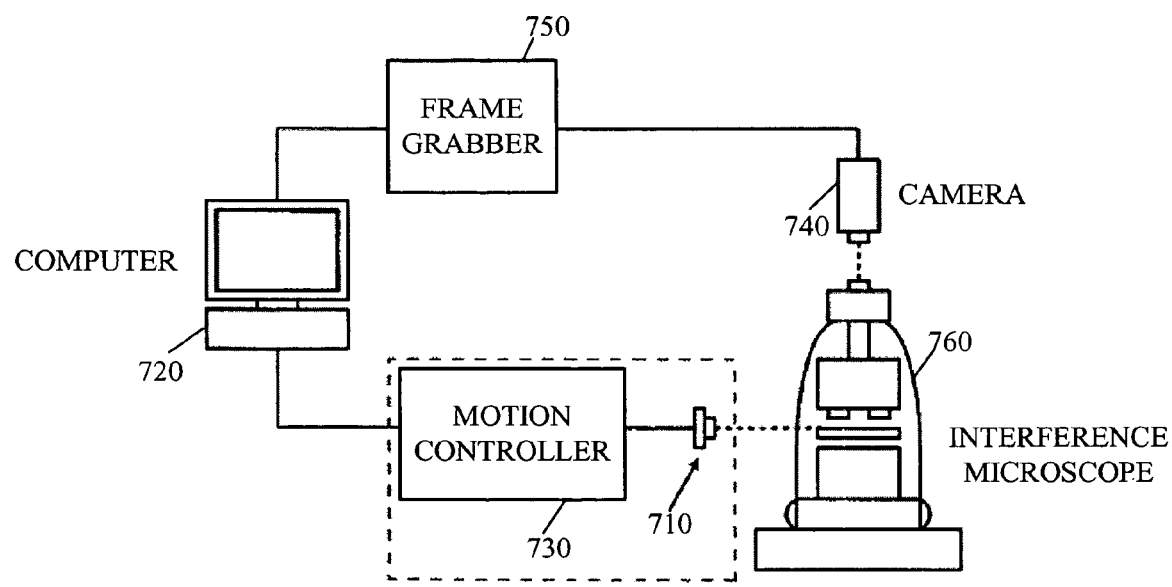
FIG. 7 is a diagram of one embodiment, among others, of a setup arrangement for performing the process of FIG. 1.

The basic setup for projection measurement is shown in FIG. 7, for some embodiments. As shown, a motorized rotation stage 710 is included to permit precise rotation of optical fiber samples about the longitudinal axis, which facilitates rapid measurement of projections at multiple angles over a full 360 degrees. The rotation stage 710 is controlled by a computer 720 through a motion controller 730. The camera 740, computer 730 with frame grabber card 750, and interference microscope 760 are optimized to ensure low-noise interference images can be obtained rapidly. A high-resolution scientific-grade digital camera (e.g., a charge coupled device camera) is preferably used to acquire the resulting interference images, which are then transmitted to a computer for storage. With the automated measurement configuration, shown in FIG. 7, multiple images can be captured at each projection angle and averaged to reduce noise effects.

Using an interference microscope to conduct measurements has the additional advantage of reducing refraction effects. As mentioned previously, optical fiber samples ought to be surrounded with an accurately known index matching oil whose refractive index value is close to (but not equal to) that of the sample outer cladding. Matching the indices of the oil and cladding lowers the deviation of the rays at the surface boundaries. Direct use of high magnification oil-immersion objectives ensures the matching criteria are be met and eliminates the need for microscope slides and cover slips that can introduce wavefront distortion. In situations where the index value of the cladding is not known, oils with different refractive indices can be tried until a suitable fringe field is observed. In addition to enabling precise matching, the microscopy approach presented corrects for some refraction effects when the system is properly focused on the center of the fiber. Even with the two corrective measures suggested, samples such as graded-index and air-silica microstructure optical fiber would not meet the parallel projection criteria due to excessive ray refraction over their transverse cross-sections. However, since one principal concern is primarily with measuring small perturbations in index profiles of commercial telecommunications fiber, refraction effects due to asymmetry are expected to be below those due to interfaces (oil/cladding and core/cladding). In cases of excessive refraction, a different form than parallel projections may be adopted in describing ray paths through the sample (for example, a fan-beam projection, among others). Ray tracing offers one method for investigating whether a particular optical fiber sample would introduce too much deviation.

Figure 8:
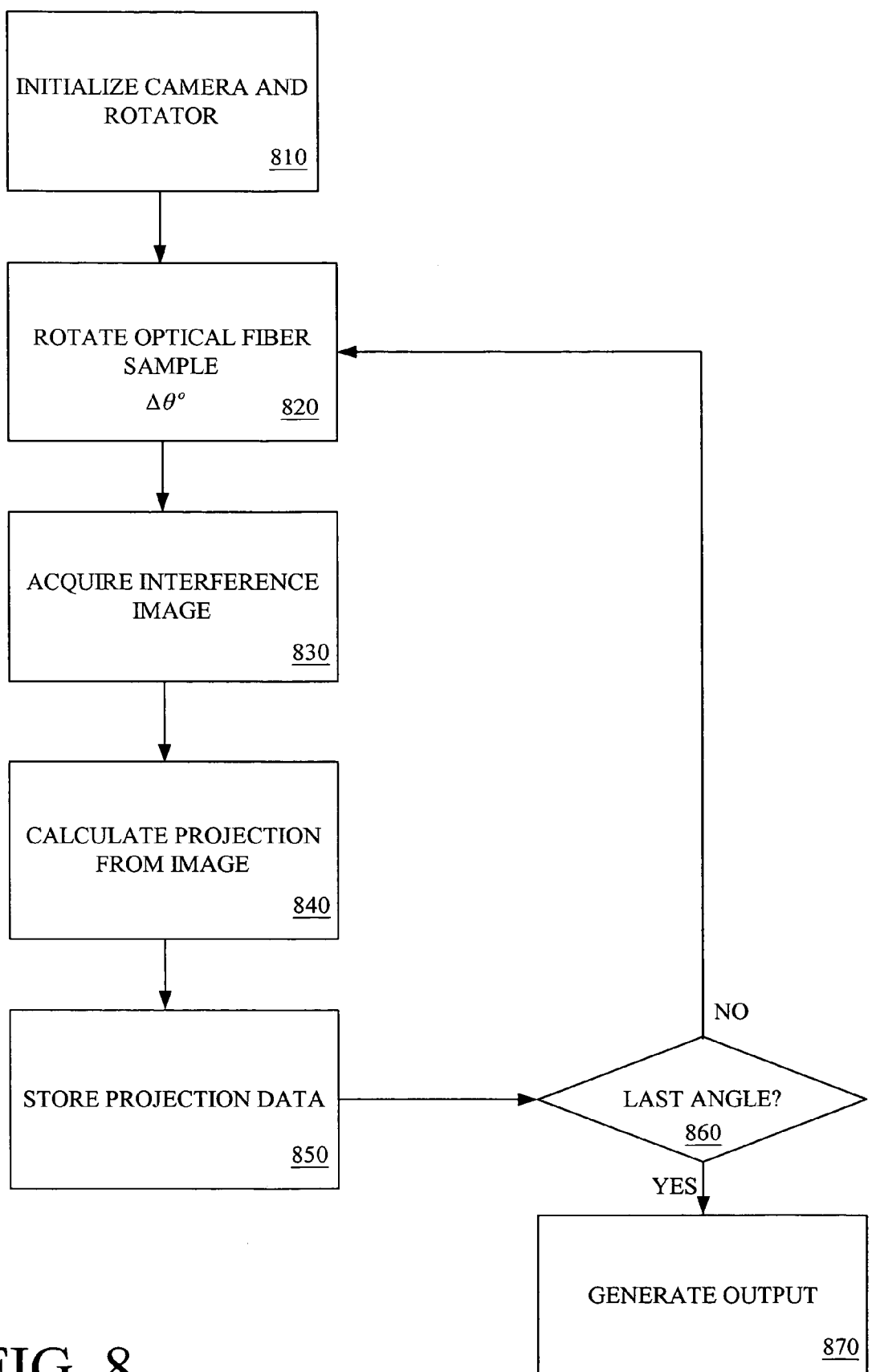
FIG. 8 is flowchart diagram of one embodiment, among others, of a procedure for acquiring projection data in accordance with the process of FIG. 1.

FIG. 8 shows a diagram of one embodiment, among others, of a procedure for acquiring the required projection data. After initializing (810) the rotation stage and camera, the optical fiber sample is rotated (820) by an angular step $\Delta\theta°$ (angular separation between projections). Several interference images are captured or acquired (830) using the frame grabber and averaged to generate a single image. Any additional, required image processing (filtering, scaling, etc.) can also be conducted at this stage. From the single processed image, an index projection (filtering, scaling, etc.) is calculated (840) and stored (850) for later use in object reconstruction. If the projection calculation portion of the procedure requires extensive time (e.g., exceeding approximately ten seconds), that portion is conducted later and only the image(s) acquired and saved at this stage. The rotation/acquisition/calculation process is repeated (860) until projection measurements of the sample have been taken over 360 degrees and the output is generated (870).

Consistent with the advantageous purpose of detecting small index variations (e.g., about $1 \times 10^{-4}$) in small objects (about 125 µm diameter), several portions of the MIOPT procedures can be changed within the reconstruction process to lower noise levels and subsequently improve detection of small variations in refractive index. Taking additional projections; and employing various reconstruction filters all act to lower noise levels in certain regions of reconstructed objects. Note, taking projections 360 degrees around the sample object, instead of over just 180 degrees, increases averaging of noisy data and reduces asymmetric ringing effects. Increasing the total number of projections (decreasing the angle between projections) also leads to increased averaging of noisy data. Altering the reconstruction filter (part of the filtered backprojection algorithm) to introduce averaging and attenuation of higher frequencies lowers the noise level and improves the chances of detecting small variations within interior regions, but not near edges or sharp transitions.

By incorporating all or some of the aforementioned additions and alterations into the MIOPT process, the ability to detect small, asymmetric index changes is improved. Accordingly, one unique feature of MIOPT among the various existing profiling techniques is that it may be purposefully designed to characterize small, asymmetric index perturbations in optical fibers and fiber devices.

As shown, MIOPT encompasses a non-destructive process for obtaining high-resolution and high-accuracy cross-sectional refractive-index profiles of small objects that potentially possess asymmetry. High-resolution applies both to spatial (better than 0.5 µm) and refractive-index (better than $1 \times 10^{-5}$) parameters. Similarly, high-accuracy refers to both spatial dimensions (within+/−1 µm) and absolute refractive-index values (less than 1% error over the profile). Though combining microinterferometry and tomography for profile measurement may seem apparent, it is not obvious that such a combination yields profiles possessing high resolution and high accuracy. In fact, no current measurement techniques can produce quantitative refractive-index profiles of azimuthally asymmetric fibers of fiber devices with sufficient resolution and accuracy. Thus, there has been a long-standing need for a non-destructive technique that is capable profiling azimuthally asymmetric optical fibers with high-resolution and high-accuracy. For example, the azimuthal asymmetry present in certain optical fibers and fiber devices, such as photonic crystal fiber and microstructure fiber, significantly influences their performance.

There are many additional aspects to the technique and its successful realization that require more than just a direct combination of the two. The difficulties and complexities associated with implementing microinterferometry and tomography alone suggest that any technique combining the two will not permit high-resolution and high-accuracy index profile measurements. For instance, the difficulties of acquiring stable interference images of objects are well known and no commercial instrument has been produced in approximately the last 25 years that is capable of generating interference images suitable for yielding projections that can be used for high-resolution reconstruction.

Further, based on available discussions in the relevant literature and measurement results published to date, it could be concluded that combining microinterferometry and tomography to conduct measurements will not enable high-resolution and high-accuracy profiling. As such, there have been no successful high-resolution, high-accuracy profile measurements of any azimuthally asymmetric fibers using techniques that combine microinterferometry and tomography. Any reported results are for fiber or fiber devices possessing azimuthal symmetry despite the ready availability of asymmetric equivalents. For instance, the noisy profile results presented by Witold Gorski in 2004 are of an azimuthally symmetric multimode optical fiber. These are but a few of the advantages of the embodiments of the present disclosure.

It should be emphasized that the above-described embodiments of the present disclosure are merely possible examples of implementations, merely set forth for a clear understanding of the principles of the disclosure. Many variations and modifications may be made to the above-described embodiments without departing substantially from the spirit and principles of the present disclosure. All such modifications and variations are intended to be included herein within the scope of this disclosure and protected by the following claims.

Therefore, at least the following is claimed:

1. A system for constructing a profile of an optical device, comprising:
   an interferometer device used to collect interference images of a sample object at a sequence of angles around the sample object;
   a projection generator to produce projections of the sample object from the interference images at the sequence of angles; and
   a tomographic device to construct the profile of the optical device from the projections of the interference images, wherein the profile is capable of characterizing small index variations of less than $1 \times 10^{-4}$ for the sample object.

2. The system of claim 1, wherein the projection generator comprises:
   a high-resolution camera to capture each of the interference images of the sample object at the sequence of angles;
   an image storing application to store each of the captured images; and
   an image processing application for calculating projection data from the captured images.

3. The system of claim 1, wherein the sequence of angles covers a 360 degree revolution around the sample object.

4. The system of claim 1, wherein the interferometer device comprises a Mach-Zehnder two-objective, transmitted-light interference microscope.

5. The system of claim 1, further comprising:
   a controller device to rotate the sample object to enable acquisition of the interference images; and
   a motorized rotation stage, under the control of the controller device, the motorized rotation stage rotating the sample object around its longitudinal axis to enable acquisition of interference images at the sequence of angles around the object.

6. The system of claim 1, wherein the profile is characterized by a spatial resolution of better than $5 \times 10^{-7}$ meters and a refractive-index resolution of better than $1 \times 10^{-5}$.

7. The system of claim 6, wherein a diameter of the sample object is less than $1 \times 10^{-3}$ meters.

8. A system for constructing a profile of a sample object, comprising:
   means for acquiring multiple projections in a range exceeding 180 degrees around the sample object; and
   means for constructing a profile of the sample object from the multiple projections, wherein the profile is capable of characterizing small index variations of less than $1 \times 10^{-4}$ the sample object.

9. A method for constructing a profile of a sample object, comprising the steps of:
   acquiring multiple projections in a range exceeding 180 degrees around the sample object; and constructing a profile of the sample object from the multiple projections, wherein the profile is capable of characterizing small index variations of less than $1 \times 10^{-4}$.

10. The method of claim 9, wherein the size of the sample object is less than $1 \times 10^{-3}$ meters in diameter.

11. The method of claim 9, further comprising the step of:
acquiring interference images around the range; and
storing the interference images as recorded images, the recorded images having a size greater than 1 megapixel.

12. The method of claim 9, further comprising the step of: averaging the recorded images to reduce noise effects.

13. The method of claim 9, wherein more than 180 projections are acquired in the range.

14. The method of claim 9, further comprising the step of: automatically rotating the sample object by an angular step to facilitate the acquisition of interference images around the range.

15. The method of claim 14, wherein the angular step is less than 1 degree.

16. The method of claim 15, wherein the range comprises a 360 degree range around the sample object.

17. The method of claim 9, wherein the profile is generated in a non-destructive manner with regard to the sample object.

18. The method of claim 9, wherein the profile is characterized by a spatial resolution of better than $5 \times 10^{-7}$ meters.

19. The method of claim 9, wherein the profile is characterized by a refractive-index resolution of better than $1 \times 10^{-5}$.

20. The method of claim 9, wherein the profile is characterized by a spatial resolution of better than $5 \times 10^{-7}$ meters and a refractive-index resolution of better than $1 \times 10^{-5}$.

* * * * *

UNITED STATES PATENT AND TRADEMARK OFFICE
CERTIFICATE OF CORRECTION

| | | |
|---|---|---|
| PATENT NO. | : 7,352,474 B2 | Page 1 of 1 |
| APPLICATION NO. | : 11/040418 | |
| DATED | : April 1, 2008 | |
| INVENTOR(S) | : Brent L. Bachim et al. | |

It is certified that error appears in the above-identified patent and that said Letters Patent is hereby corrected as shown below:

Col. 1, line 12, before "TECHNICAL FIELD", insert

--STATEMENT REGARDING FEDERALLY SPONSORED RESEARCH OR DEVELOPMENT

This invention was made with Government support under agreement number MDA972-99-1-0002 awarded by the Defense Advanced Research Projects Agency (DARPA). The Government has certain rights in this invention.--

Signed and Sealed this

Twenty-second Day of July, 2008

JON W. DUDAS
*Director of the United States Patent and Trademark Office*